US006610890B1

(12) United States Patent
Garcia de Quesada Fort et al.

(10) Patent No.: US 6,610,890 B1
(45) Date of Patent: Aug. 26, 2003

(54) ALDOSE REDUCTASE INHIBITORS AND PHARMACEUTICAL COMPOSITIONS

(75) Inventors: Teresa Garcia de Quesada Fort, Tres Cantos (ES); Jesús A De La Fuente Blanco, Madrid (ES); Ma Jesús Martin Lopez, Tres Cantos (ES); Isabel Reymundo Cuesta, Madrid (ES)

(73) Assignee: O.N.C.E.-(Organizacion Nacional De Cicgos) (ES)

( * ) Notice: Subject to any disclaimer, the term of this patent is extended or adjusted under 35 U.S.C. 154(b) by 0 days.

(21) Appl. No.: 10/040,337

(22) Filed: Jan. 7, 2002

Related U.S. Application Data

(63) Continuation of application No. 09/857,854, filed on Jun. 11, 2001, now abandoned.

(30) Foreign Application Priority Data

Dec. 11, 1998 (EP) ................................ 9827391
Dec. 13, 1999 (WO) ............................ PCT/GB99/04190

(51) Int. Cl.[7] .................. C07C 49/76; C07C 41/00; C07C 39/16; C07C 15/12; A01N 31/00
(52) U.S. Cl. .................. 568/332; 568/637; 568/638; 568/639; 568/723; 568/726; 585/25; 514/686; 514/717; 514/765; 514/730; 514/738
(58) Field of Search .................. 568/332, 637, 568/638, 639, 723, 726; 585/25; 514/686, 717, 765, 730, 738

(56) References Cited

U.S. PATENT DOCUMENTS 3,786,022 A    1/1974    Hata et al. .................. 260/47
3,912,782 A  * 10/1975   Kiel et al. .................. 260/620
5,202,355 A    4/1993    Nakatsu .................. 514/568

FOREIGN PATENT DOCUMENTS

EP    0 470 832 A2    12/1992    .................. 59/64

OTHER PUBLICATIONS

Chemical Abstracts, vol. 97, No. 5, (Aug. 2, 1982) Columbus, Ohio, US; abstract No. 33363b, H. Ono: "2,2',4,4'—Tetrahydroxybenzophenone as a New Aldose Reductase Inhibitor", p. 44; col. 2; XP002131322 abstract & *Nippon Ganka Gakkai Zasshi,* vol. 86, No. 4, (1982), pp. 353–357.
Hawkins, "Degradation of Novolak Resins", *J. Appl. Chem.,* vol. 6, (1956), pp. 131–139.
Ono et al., "2,2',4,4'—Tetrahydroxybenzophenone as a New Aldose Reductase Inhibitor", *Nippon Ganka Gakkai Zasshi,* vol. 86, No. 4, (1982), pp. 353–357.

* cited by examiner

*Primary Examiner*—Johann Richter
*Assistant Examiner*—Sikarl A. Witherspoon
(74) *Attorney, Agent, or Firm*—Fish & Richardson P.C.

(57) ABSTRACT

Medicaments for treating diabetic complications contain a compound of formula (A), wherein at least one Y or one Y' is OH, and the remainder are selected from H, Hal, OH, OMe and $NO_2$; X is O, S, keto or a direct link (A)

26 Claims, No Drawings

ALDOSE REDUCTASE INHIBITORS AND PHARMACEUTICAL COMPOSITIONS

CROSS-REFERENCE TO RELATED APPLICATIONS

This application is a continuation of commonly owned U.S. patent application Ser. No. 09/857,854, filed Jun. 11, 2001, now abandoned, which application claimed priority under 35 U.S.C. §371 of commonly owned PCT Application No. PCT/GB99/04190, filed Dec. 13, 1999, which application claimed priority of commonly owned British Patent Application No. 9827391.5, filed Dec. 11, 1998. The PCT application designated the United States and was published in the English language on Jun. 22, 2000 as WO 00/35848.

The present invention provides the use, as Aldose Reductase Inhibitors (ARIs), for the manufacture of a medicament for the treatment and/or prevention of diabetic complications, of a compound represented by the following general formula (A)

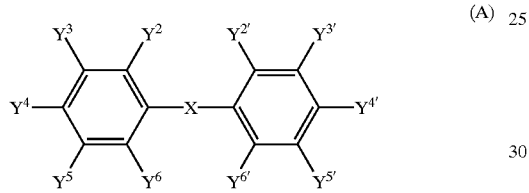

(A)

wherein at least one of Y or Y' is OH and the others Y and Y' are independently selected from the group consisting of hydrogen, halogen, hydroxy, methoxy, and nitro; X is selected from the group consisting of O, S, and ketone, or both substituted benzyl groups are directly linked as a substituted biphenyl compound.

In addition, these aldose reductase inhibitors can form salts with a pharmaceutically acceptable cation, all such salts are within the scope of this invention.

In addition, some of the compounds of this invention can form hydrates or solvates and they are also within the scope of the invention.

The present invention also provides six novel synthetic compounds having the following formula:

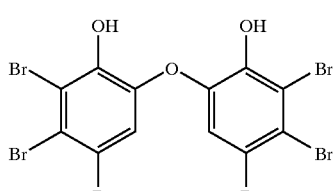

A-I

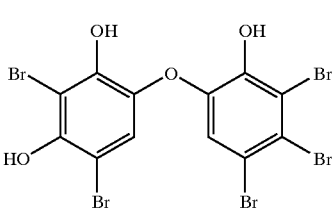

A-II

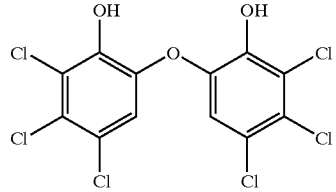

A-III

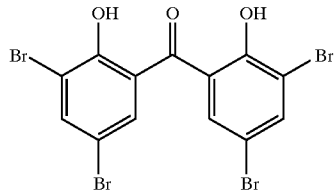

A-IV

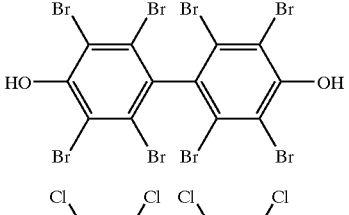

A-V

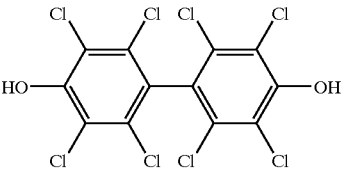

A-VI

FIELD OF THE INVENTION

The present invention is directed to novel pharmaceutical compositions, which possess Aldose Reductase inhibitory activity, and are useful for the treatment and/or prevention of diabetic complications; the present invention is also directed to novel compounds which possess Aldose Reductase inhibitory activity.

BACKGROUND OF THE INVENTION

Diabetic neuropathy, diabetic cataract and retinopathy, diabetic corneal keratopathy, diabetic nephropathy, diabetic dermopathy and other diabetic microangiopathy have been known as chronic diseases as a result of diabetes which are difficult to treat. Accumulation of intracellular sorbitol, the reduced product of glucose, catalyzed by Aldose Reductase (AR) (EC 1.1.1.21), is thought to be the cause of the development of these diabetic complications[1-3]. Accordingly, agents for inhibiting this Aldose Reductase have been thought to be effective for the therapy and the prevention of diabetic complications and have been studied[4-6]. However, despite numerous attempts over 16 years, the results of aldose reductase inhibitor (ARI) trials, with the known aldose reductase inhibitors, for the treatment of diabetic complications have not proven efficacy[7]; also, despite the apparent structural diversity of aldose reductase inhibitors (ARIs), certain common electronic and steric features have become apparent through computer modeling, molecular orbital calculations, and known structure-activity relationships, and from competition studies using different aldose reductase inhibitors (ARIs) also suggest that ARIs interact at a single common site on the enzymes[8-10].

Under these circumstances, the inventors have conducted a study looking for new compounds structurally different of the known aldose reductase inhibitors (ARIs). As a result, the present invention provides a novel class of aldose reductase inhibitors (ARIs) having the general formula (A). These compounds exhibit an excellent inhibitory activity to Aldose Reductase.

Compounds having the general formula (A) have long been known as antiseptic and antimicrobial agents[11], as cardiac agents[12], as antiinflammatory agents[13], and as inhibitors of the enzymes: protein kinase C (PKC), protein tyrosine kinase (PTK), inosine monophosphate dehydrogenase (IMPDH), guanosine monophosphate synthetase (GMPS), and 15-lipoxygenase (15-LO)[14].

Compounds having the general formula (A) have long been reported from marine sources[14-18].

SUMMARY OF THE INVENTION

The present invention provides the use, as inhibitors of Aldose Reductase, for the manufacture of a medicament for the treatment and prevention of diabetic complications, of a compound represented by the following general formula (A)

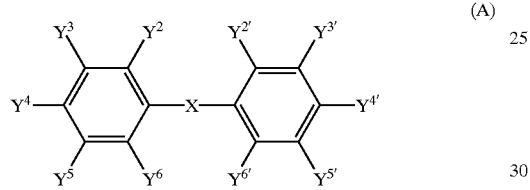

(A)

wherein at least one of Y or Y' is OH and the other Y and Y' are independently selected from the group consisting of hydrogen, halogen, hydroxy, methoxy, and nitro; X is selected from the group consisting of O, S, and ketone, or both substituted benzyl groups are directly linked as a subtituted biphenyl compound.

In addition, these aldose reductase inhibitors can form salts with a pharmaceutically acceptable cation, all such salts are within the scope of this invention.

In addition, some of the compounds of this invention can form hydrates or solvates and they are also within the scope of the invention.

The present invention further provides pharmaceutical compositions which contain as active ingredient a compound with the formula (A). Examples of pharmaceutical compositions include any solid (tablets, pills, capsules, granules, etc.) or liquid (solutions, suspensions or emulsions) with suitable formulation of oral, topical or parenteral administration, and they may contain the pure compound or in combination with any carrier or other pharmacologically active compounds. These compositions may need to be sterile when administered parenterally.

The correct dosage of a pharmaceutical composition comprising compounds with the formula (A), will vary according to the pharmaceutical formulation, the mode of application, and the particular situs, host and diabetic complication being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The present invention also provides six novel synthetic compounds having the following formula:

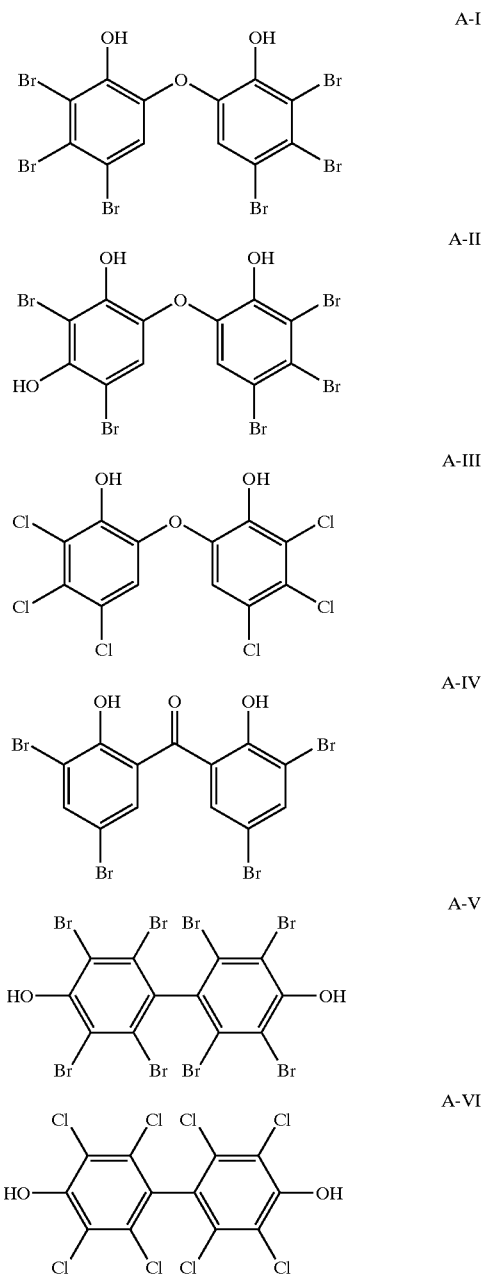

as well as a process for their preparation.

As hereunder, several examples of the methods of obtaining the compounds of the present invention are given.

EXAMPLE 1

3,3',4,4',5,5'-hexabromo-2,2'-dihydroxy-oxydiphenyl (A-I) (general formula A, where X=O, $Y^2=Y^{2'}$=OH, $Y^6=Y^{6'}$=H, and $Y^3Y^{3'}=Y^4=Y^{4'}=Y^5=Y^{5'}$=Br).

Was obtained as it is showed in Scheme 1.

Was obtained as it is showed in Scheme 2.

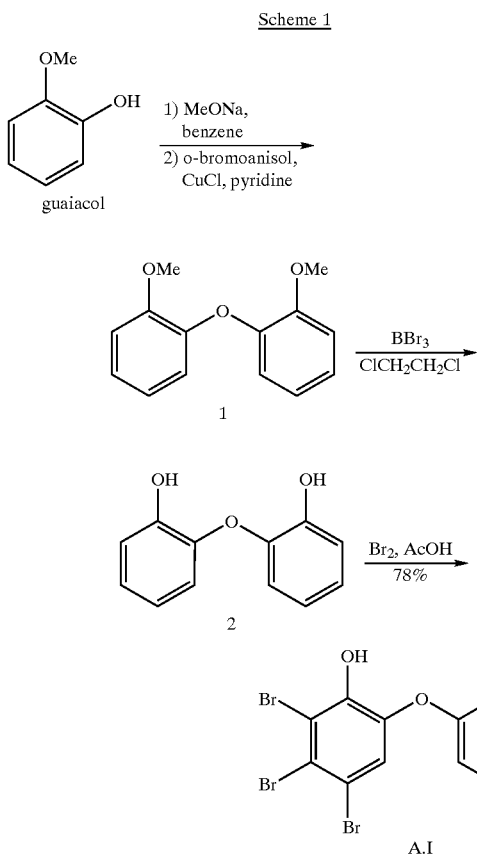

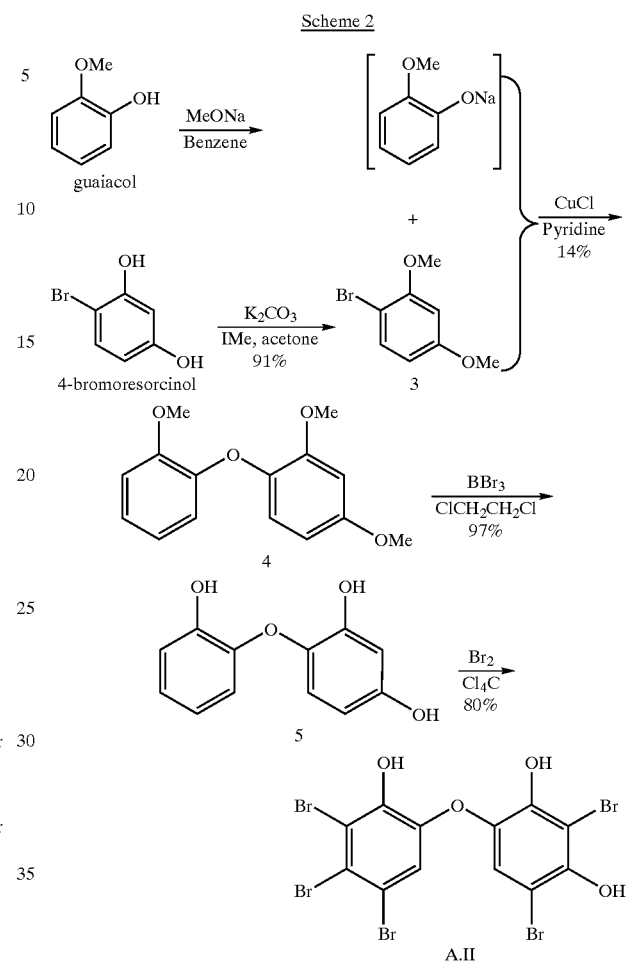

2,2'-Oxydiphenol dimethyl ether (1) was synthesized from guaiacol and o-bromoanisol as was previously described[19]. The dimethyl ether (1) was cleaved to 2,2'-oxydiphenol (2) by treatment with boron tribromide in ethylene chloride as was previously described[20]. To a solution of 2,2'-oxydiphenol (2) (0.2 g) in acetic acid (6 ml) bromine (2 ml, 40 eq) was added dropwise and with stirring. After the addition the reaction mixture was stirred at 90–95° C. for 15h. The mixture was evaporated and the residue was chromatographed on silica gel (Hex-AcOEt 7/3) to afford 3,3',4,4',5,5'-hexabromo-2,2'-dihydroxy-oxydiphenyl (A-I) (0.52 g, 78%), mp. 188–190° C. $^{13}$C-NMR (CD$_3$COCD$_3$), δ (ppm): 114.23 (s), 115.60 (s), 122.54 (d), 123.31 (s), 144.34 (s), 147.52 (s); $^1$H-NMR (CDCl$_3$), δ (ppm): 7.19 (s, 2H).

EXAMPLE 2

3,3',4',5,5'-pentabromo-2,2',4-trihydroxy-oxydiphenyl (A-II) (general formula A, where X=O, $Y^2=Y^{2'}=Y^4=OH$, $Y^6=Y^{6'}=H$, and $Y^3=Y3'=Y^{4'}=Y^5=Y^{5'}=Br$).

To a solution of 4-bromoresorcinol (0.8 g) in acetone (5 ml), at room temperature and under argon, K$_2$CO$_3$ (3.5 g, 6 eq) was added. After stirring for 30 min., methyl iodide (1.58 ml, 6 eq) was added. The reaction mixture was stirred overnight and then the solvent was evaporated off. The residue was poured into water, extracted with methylene chloride and dried over Na$_2$SO$_4$. The evaporation of the combined extracts gave a residue which was chromatographed on silica gel (Hex-AcOEt 9/1) to give (3) (0.836 g, 91%), $^{13}$C-NMR (CDCl$_3$), δ (ppm): 55.45 (q), 56.01 (q), 99.82 (d), 102.27 (s), 105.77 (d), 133.02 (d), 156.40 (s), 160.12 (s), $^1$H-NMR (CD$_3$Cl), δ (ppm): 3.78 (s, 3H), 3.85 (s, 3H), 6.38 (dd, 1H, J=8.4, 2.7 Hz), 6.47 (d, 1H, J=2.7 Hz), 7.39 (d, 1H, J=8.4 Hz).

A solution of guaiacol (0.4 g), benzene (3 ml) and sodium methoxide (0.26 g, 1.5 eq) was stirred at room temperature under argon, for 45 min. Then, the solvent was evaporated off. The residue in pyridine (4 ml) was treated with (3) (1.2 g, 1.7 eq) and copper (I) chloride (0.32 g, 1.0 eq). The reaction mixture was heated at 130° C. for 7h. The cooled solution was poured into 5M hydrochloric acid, extracted with diethyl ether and dried over Na$_2$SO$_4$. The extract was concentrated and the residue was chromatographed on silica gel (CH$_2$Cl$_2$-Hex 8/2) to give (4) (0.12 g, 14%). $^{13}$C-NMR (CDCl$_3$), δ (ppm): 55.42 (q), 55.73 (q), 55.81 (q), 100.37

(d), 103.69 (d), 112.09 (d), 116.29 (d), 120.53 (d), 120.86 (d), 122.53 (d), 138.59 (s), 147.32 (s), 149.53 (s), 151.80 (s), 156.74 (s); $^1$H-NMR (CDCl$_3$), δ (ppm): 3.78 (s, 6H), 3.89 (s, 3H), 6.40 (dd, 1H, J=8.7, 3 Hz), 6.56 (d, 1H, J=3 Hz), 6.68 (dd, 1H, J=7.8, 2.4 Hz), 6.80 (td, 1H, J=7.2, 2.4 Hz), 6.88 (d, 1H, J=8.7 Hz), 6.96 (m, 2H).

Cleavage of (4) by the same procedure as for (1) gave (5) (97%). mp: 164–160° C. $^{13}$C-NMR (CD$_3$COCD$_3$), δ (ppm): 104.71 (d), 107.31 (d), 117.02 (d), 117.34 (d), 120.46 (d), 122.03 (d), 123.89 (d), 137.22 (s), 146.91 (s), 148.12 (s), 150.27 (s), 155.54 (s); $^1$H-NMR (CD$_3$COCD$_3$), δ (ppm): 6.35 (dd, 1H, J=8.7, 2.7 Hz), 6.54 (d, 1H, J=2.7 Hz), 6.74 (m, 2H), 6.81 (d, 1H, J=8.7Hz), 6.91 (m, 2H).

To a solution of (5) (16 mg) in carbon tetrachloride (2 ml) was added bromine (1 ml). The mixture was stirred at room temperature for 24h and then evaporated in vacuo. The residue was chromatographed on silica gel (CH$_2$Cl$_2$-AcOEt 95/5) to give 3,3',4',5,5'-pentabromo-2,2',4-trihydroxy-oxydiphenyl (A-II) (36 mg, 80%). mp: 207–209° C, $^{13}$C-NMR (CD$_3$COCD$_3$), δ (ppm): 99.57 (s), 101.64 (s), 113.84 (s), 114.80 (s), 119.71 (d), 121.39 (s), 123.70 (d), 136.66 (s), 146.44 (s), 146.67 (s), 147.71 (s), 150 (s); $^1$H-NMR (CD$_3$COCD$_3$), δ (ppm): 7.13 (s, 1H), 7.35 (s, 1H).

EXAMPLE 3

3,3',4,4',5,5'-Hexachloro-2,2'-dihydroxy-oxydiphenyl (A-III) (general formula A, where X=O, Y$^2$=Y$^{2'}$=OH, Y$^6$=Y$^{6'}$=H, and Y$^3$=Y$^{3'}$=Y$^4$=Y$^{4'}$=Y$^5$=Y$^{5'}$=Cl).

Was obtained as it is showed in Scheme 3.

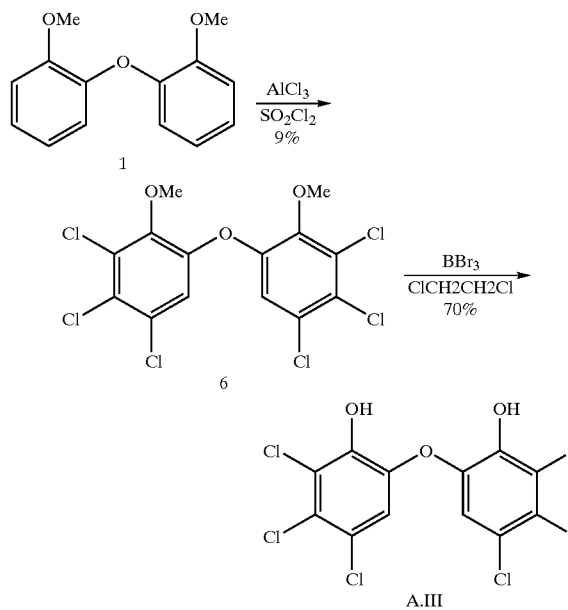

Scheme 3

To a solution of (1) (60mg), in SO$_2$Cl$_2$ (1 ml) was added AlCl$_3$ (19 mg, 0.5 eq). The reaction mixture was stirred at 95° C. for 5h and then evaporated off The crude is poured in water, extracted with AcOEt and the extract dried over Na$_2$SO$_4$. Evaporation of the solvent gave a crude which was chromatographed on silica gel (Hex-AcOEt 95/5) to afford (6) (10 mg, 9%). $^1$H-NMR (CDCl$_3$), δ (ppm): 3.90 (s, 6H), 6.94 (s, 2H).

The dimethyl ether (6) was cleaved by treatment with boron tribromide in ethylene chloride by the same procedure as for (1) to afford 3,3',4,4',5,5'-hexachloro-2,2'-dihydroxy-oxydiphenyl (A-III) (70%). $^{13}$C-NMR (CD$_3$COCD$_3$), δ (ppm): 119.26 (d), 122.12 (s), 123.08 (s), 127.52 (2), 144.43 (s), 146.79 (s); $^1$H-NMR (CD$_3$COCD$_3$), δ (ppm): 7.28 (s, 2H).

EXAMPLE 4

3,3',5,5'-tetrabromo-2,2'-dihydroxybenzophenone (A-IV) (general formula A, where X=CO, Y$^2$=Y$^{2'}$=OH, Y$^4$=Y$^{4'}$=Y$^6$=Y$^{6'}$=H, and Y$^3$=Y$^{3'}$=Y$^5$=Y$^{5'}$=Br).

Bromination of 2,2'-dihydroxybenzophenone by the same procedure as for (2), followed by chromatography of the crude on silica gel (Hex-Diethyl ether 8/2) gave 3,3',5,5'-tetrabromo-2,2'-dihydroxybenzophenone (A-IV) (96%). mp: 179.180° C. $^{13}$C-NMR (CD$_3$COCD$_3$), δ (ppm): 111.76 (s), 113.24 (s), 125.40 (s), 133.60 (d), 140.34 (d), 155.12 (s), 198.93 (s), $^1$H-NMR (CDCl$_3$), δ (ppm): 7.54 (d, 2H, J=2.4 Hz), 7.92 (d, 2H, J=2.4 Hz).

EXAMPLE 5

2,2',3,3',5,5',6,6'-Octabromo-4,4'-biphenol (A-V) (general formula A, where X=nothing, Y$^4$=Y$^{4'}$=OH, and Y$^2$=Y$^{2'}$=Y$^3$=Y$^{3'}$=Y$^5$=Y$^{5'}$=Y$^6$Y$^{6'}$=Br).

4,4'-Biphenol was treated with MeI by the same procedure as for o-bromoresorcinol to give 4,4'-dimethoxybiphenyl (98%). $^{13}$C-NMR (CDCl$_3$), δ (ppm): 55.32 (q), 114.13 (d), 127.70 (d), 133.44 (s), 158.65 (s); $^1$H-NMR (CDCl$_3$), δ (ppm): 3.85 (s, 6H), 6.96 (d, 4H, J=8.4 Hz), 7.49 (d, 4H, J=8.4 Hz).

To a solution of 4,4'-dimethoxybiphenyl (30 mg) in bromine (1 ml) was added iron powder (56 mg). The suspension was stirred at 80° C. for 3h. The cooled solution was poured into water, extracted with chloroform and dried with Na$_2$SO$_4$. Evaporation of the organic layers gave a residue which was chromatographed on silica gel (Hex-AcOEt 7/3) to afford 2,2',3,3',5,5',6,6'-Octabromo-4,4'-biphenol (A-V) (90 mg, 78%). mp: 282° C.; $^{13}$C-NMR (CD$_3$COCD$_3$), δ (ppm): 114.66 (s), 127.37 (s), 138.83 (s), 153.94 (s); EI m/z 817 (15%).

EXAMPLE 6

2,2',3,3',5,5',6,6'-Octachloro-4,4'-biphenol (A-VI) (general formula A, where X=nothing, Y$^4$=Y$^{4'}$=OH, and Y$^2$=Y$^{2'}$=Y$^3$=Y$^{3'}$=Y$^5$=Y$^{5'}$=Y$^6$=Y$^{6'}$=Cl).

To a solution of SO$_2$Cl$_2$ (3 ml) and AlCl$_3$ (0.036 g, 0.5 eq), under reflux, was added dropwise, a mixture of 4,4'-biphenol (100 mg), S$_2$Cl$_2$ (95 mg, 1.3 eq) and SO$_2$Cl$_2$ (5 ml). After the addition, the reaction was stirred under reflux for 7h. The cooled solution was evaporated off to give a crude which was poured into AcOEt, washed with brine and dried over Na$_2$SO$_4$. Evaporation of the organic layer gave a crude which was chromatographed on silica gel to afford 2,2',3, 3',5,5',6,6'-octachloro-4,4'-biphenol (A-VI) (40 mg, 16%).mp: 94–96° C., $^{13}$C-NMR (CD$_3$COCD$_3$), δ (ppm): 92.69 (s), 132.2 (s), 146.18 (s), 168.48 (s).

EXAMPLE 7

2,2',3,3',5,5',6,6'-Octafluoro-4,4'-biphenol hydrate (A-VII) (general formula A, where X=nothing, Y$^4$=Y$^{4'}$=OH, and Y$^2$=Y$^{2'}$=Y$^3$=Y$^{3'}$=Y$^5$=Y$^{5'}$Y$^6$=Y$^{6'}$=F).

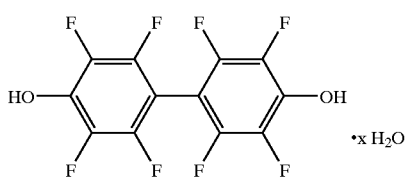

A-VII

This compound is a commercial product (Aldrich Chemical Co., ref.37,876–3).

PHARMACOLOGICAL ACTION OF THE COMPOUNDS OF THE PRESENT INVENTION

1) Action of Inhibiting Human Recombinant Aldose Reductase

Human recombinant aldose reductase was obtained and purified as previously described[21] with slight modifications. Briefly, Sf9 insect cells (*Spodoplera frugiperda*, from Pharmingen) were cultured in Grace's medium (Gibco) at 27° C. Then, cultures were infected with the purified recombinant baculovirus AcAR[22] that was kindly provided by Dr. C. Nishimura (National Children's Medical Research Center, Tokyo, Japan). The enzyme released into the culture medium was purified by affinity chromatography (Matrex Gel Orange A, Amicon). This Aldose Reductase was kept at −20° C. in 50 mM sodium phosphate, pH 7.0, 5 mM dithiotreitol and 50% glycerol.

Recombinant Aldose Reductase activity was determined according to the method previously described[21]. The assay was carried out in a 96-well microtiter plate, at 37° C. in 100 mM sodium phosphate buffer, pH 6.2, 400 mM $(NH_4)_2SO_4$, 0.1 mM NADPH and 5 mU/ml recombinant aldose reductase (1 mU of activity was defined as a change in absorbance of 0.012 units per minute). The reaction was initiated by addition of 10 mM glyceraldehyde and the enzymatic activity measured as the NADPH disappearance at 340 nm in a plate reader (MR-5000, Dynatech). Compounds were dissolved in DMSO (1% final concentration).

2) Action of Inhibiting the Intracellular Accumulation of Sorbitol in Rabbit Cornea Cells For this assay, cells from rabbit cornea (ATCC CCL 60) were used as previously described[23]. In summary, 10×10[6] cells were incubated in 2.5 ml of Minimum Essential Medium (JRH Biosciences), 0.5% foetal calf serum and 50 mM glucose for 16 h at 37° C. in presence of 5% $CO_2$. Compounds under study were added in DMSO whose final concentration was 1%. The sorbitol accumulated in the cells was extracted by lysis with 8% perchloric acid and neutralised with 2N KOH[24]. Sorbitol quantitation was carried out using a calorimetric test (D-Sorbitol/Xylitol, Boehringer Mannheim).

Examples of the activity results are given in Table 1.

TABLE 1

| COMPOUND | INHIBITION, $IC_{50}$ ($\mu$M) | |
|---|---|---|
| | Aldose Reductase | Sorbitol Accumulation |
| A-I | 4.00 | 1.00 |
| A-II | 2.00 | 8.00 |
| A-III | 5.00 | 0.24 |

TABLE 1-continued

| COMPOUND | INHIBITION, $IC_{50}$ ($\mu$M) | |
|---|---|---|
| | Aldose Reductase | Sorbitol Accumulation |
| A-IV | 4.00 | 5.00 |
| A-V | 1.00 | >12 |
| A-VI | 11.00 | 0.22 |
| A-VII | 0.22 | 0.42 |

REFERENCES

The following references provide background information related to the present invention:

1) Kador, P. F. *Med Res. Rev.* 1988, 8, 325–352.
2) Tanimoto, T., Nishimura, C. *Peripheral Nerve* 1993, 4, 149–158.
3) Dvornik, D. *In Aldose Reductase Inhibition: An Approach to the Prevention of Diabetic Complications*; Porte D.Ed.; McGraw-Hill: New York, 1987.
4) Kotani, T.; Nagaki, Y.; Ishii, A.; Konishi, Y.; Yago, H.; Suehiro, S.; Okukado, N.; Okamoto, K. *J Med. Chem.* 1997, 40, 684–694, and references therein.
5) Kador, P. F.; Kinoshita, J. H.; Sharpless, N. E. *J Med. Chem.* 1985, 28, 841–849.
6) Kador, P. F.; Robinson, W. G.; Kinoshita, J. H. *Annu. Rev. Pharmacol. Toxicol.* 1985, 25, 691–714.
7) Pfeifer, M. A.; Schumer, M. P.; Gelber, D. A. *Diabetes* 1997, 46 (Suppl.2), S82–S89.
8) Lee, Y. S.; Pearstein, R.; Kados, P. F. *J. Med Chem.* 1994, 37, 787–792.
9) Kador, P. F.; Sharpless, N. E. *Mol. Pharmacol.* 1983, 24, 521–531.
10) Kador, P. F.; Nakayama, T.; Sato, S. Smar, M.; Miller, D. D. *Enzymology and Mol. Biol. of Carb. Metabol.* 2 1989, 237–250.
11) Higa, T.; Fujiyama, T.; Scheuer, P. J. *Comp. Biochem. Physiol.* 1980, 65B, 525.
12) Endo, M.; Nakagawa, M.; Hamamoto, Y.; Ishihama M. *Pure & Appl. Chem.* 1986, 58, 387.
13) Kuniyoshi, M.; Yamada, K.; Higa, T. *Experientia* 1985, 41, 523
14) Fu, X.; Schmitz, F. J.; Govindan, M.; Abbas, S. A. *J. Nat. Prod.* 1995, 58, 1384–1391.
15) Sharma, G. M.; Vig, B. *Tetrahedron Lett.* 1972, 17, 1715–1718.
16) Norton, R. S.; Croft, K. D.; Wells, R. J. *Tetrahedron*, 1981, 37, 2341–2349.
17) Carte, B.; Faulkner, D. J. *Tetrahedron*, 1981, 37, 2335–2339.
18) Fu, X.; Schmitz, F. J. *J. Nat. Prod.* 1996, 59, 1102–1103.
19) Kime, D. E.; Norymberski, J. K. *J. Chem. Soc., Perkin Trans* 1 1977, 1048.
20) Francesconi. K. A.; Ghisalberti, E. L. *Aust. J. Chem.* 1985, 38, 1271–7.
21) Nishimura, C.; Yamaoka, T., Mizutani, M.; Yamashita, K.; Akera, T.; Tanimoto, T. *Biochim. Biophys. Acta* 1991, 1078, 171–178.
22) Nishimura, C., Matsuura, Y., Kokai, Y.; Akera, T.; Carper, D.; Moijana, N.; Lyons, C.; Flynn, T. G. *J. Biol. Chem.* 1990, 265, 9788–9792.
23) Rink, H., Baumstark-Khan, C. In: "*Manual of Oculotoxicity*". Eds. O. Hockwin, K. Green, L. F. Rubin; Gustav Fischer Verlag, Stuttgart, Germany, 1992, pp. 389–401.
24) Yaginuma, S., Asahi, A., Takada, M., Hayashi, M., Tsujino M. & Mizuno, K. In: "*Novel Microbial Products* for Medicine and Agriculture", Eds. A. L. Demain, G. A. Somkuti, J. C. Hunter-Cevera, H. W. Rossmore; Society for Industrial Microbiology, 1989, pp. 127–133.

What is claimed is:

1. A compound according to the general formula (A)

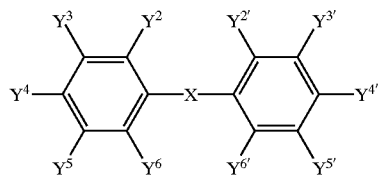

where X=O, $Y^2=Y^{2'}=OH$, $Y^6=Y^{6'}=H$, and $Y^3=Y^{3'}=Y^4=Y^{4'}=Y^5=Y^{5'}=Br$.

2. A compound according to the general formula (A)

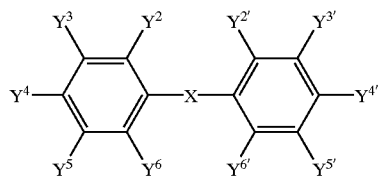

where X=O, $Y^2=Y^{2'}=Y^4=OH$, $Y^6=Y^{6'}=H$, and $Y^3=Y^{3'}=Y^{4'}=Y^5=Y^{5'}=Br$.

3. A compound according to the general formula (A)

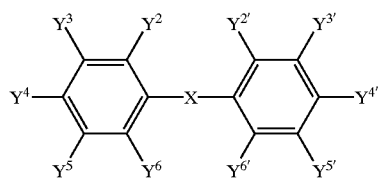

where X=O, $Y^2=Y^{2'}=OH$, $Y6=Y^{6'}=H$, and $Y^3=Y^{3'}=Y^4=Y^{4'}=Y^5=Y^{5'}=Cl$.

4. A pharmaceutical composition for the treatment and/or prevention of diabetic complications comprising as an active ingredient a compound, or a pharmaceutically acceptable salt thereof, according to the general formula (A)

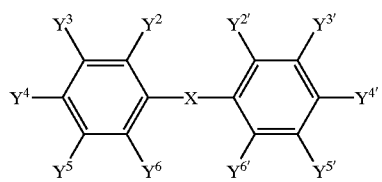

where X=CO, $Y^2=Y^{2'}=OH$, $Y^4=Y^{4'}=Y^6 50 Y^{6'}=H$, and $Y^3=Y^{3'}=Y^5=Y^{5'}=Br$.

5. A pharmaceutical composition for the treatment and/or prevention of diabetic complications comprising as an active ingredient a compound, or a pharmaceutically acceptable salt thereof, according to the general formula (A)

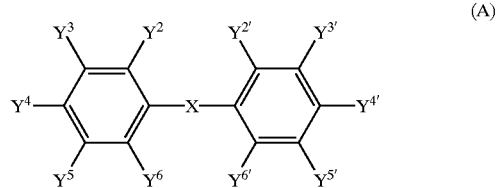

where X= a single bond directly linking both substituted benzyl groups, $Y^4=Y^{4'}=OH$, and $Y^2=Y^{2'}=Y^3=Y^{3'}=Y^5=Y^{5'}=Y^6=Y^{6'}=Br$.

6. A pharmaceutical composition for the treatment and/or prevention of diabetic complications comprising as an active ingredient a compound, or a pharmaceutically acceptable salt, hydrate or solvate thereof, according to the general formula (A)

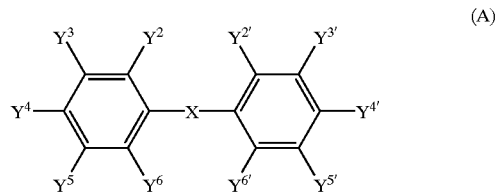

where X= a single bond directly linking both substituted benzyl groups, $Y^4=Y^{4'}=OH$, and $Y^2=Y^{2'}=Y^3=Y^{3'}=Y^5=Y^{5'}=Y^6=Y^{6'}=Cl$.

7. A method of treating diabetic complications in mammals comprising the administration of a compound represented by the following general formula (A)

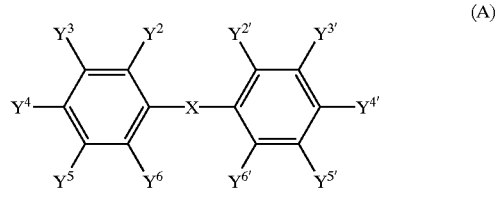

or a pharmaceutically acceptable salt, hydrate or sovate therof, wherein at least one of Y or Y' is OH;

the others Y and Y' are independently selected from the group consisting of hydrogen, halogen, hydroxy, methoxy, and nitro; and X is selected from the group consisting of O, S, ketone, and a single bond directly linking both substituted benzyl groups.

8. The method of claim 7, wherein the diabetic complications comprise diabetic neuropathy, diabetic cataract and retinopathy, diabetic corneal keratopathy, diabetic nephropathy, diabetic dermopathy and other diabetic microangiopathics.

9. A method of treating diabetic complications in mammals comprising the administration of a compound represented by the following general formula (A)

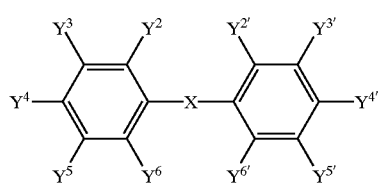

or a pharmaceutically acceptable salt, hydrate or solvate thereof, wherein at least one of Y or Y' is OH;

at least one of Y or Y' is a halogen;

the others Y and Y' are independently selected from the group consisting of hydrogen, halogen, hydroxy, methoxy, and nitro; and X is selected from the group consisting O, S, ketone, and a single bond directly lining both substituted benzyl groups.

10. The method of claim 9, wherein the diabetic complications comprise diabetic neuropathy, diabetic cataract and retinopathy, diabetic corneal keratopathy, diabetic nephropathy, diabetic dermopathy and other diabetic microangiopathies.

11. A method of treating diabetic complications in mammals comprising the administration of a compound represented by the following general formula (A)

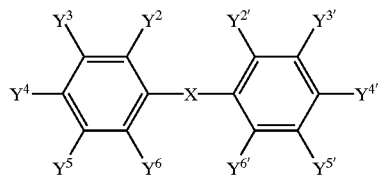

or a pharmaceutically acceptable salt, hydrate or solvate thereof, wherein at least one of Y or Y' is OH;

the others Y and Y' are independently selected from the group consisting of hydrogen, halogen, hydroxy, methoxy, and nitro; and

X=O.

12. The method of claim 11, wherein the diabetic complications comprise diabetic neuropathy, diabetic cataract and retinopathy, diabetic corneal keratopathy, diabetic nephropathy, diabetic dermopathy and other diabetic microangiopathies.

13. A method of treating diabetic complications in mammals comprising the administration of a compound represented by the following general formula (A)

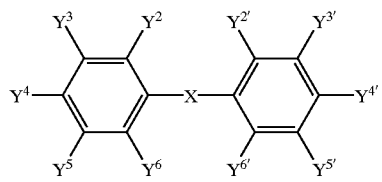

or a pharmaceutically acceptable salt, hydrate or solvate thereof wherein at least one of Y or Y' is OH;

the others Y and Y' are independently selected from the group consisting of hydrogen, halogen, hydroxy, methoxy, and nitro; and X is a single bond directly linking both substituted benzyl groups.

14. The method of claim 13, wherein the diabetic complications comprise diabetic neuropathy, diabetic cataract and retinopathy, diabetic corneal keratopathy, diabetic nephropathy, diabetic dermopathy and other diabetic microangiopathies.

15. A method of treating diabetic complications in mammals comprising the administration of a compound represented by the following general formula (A)

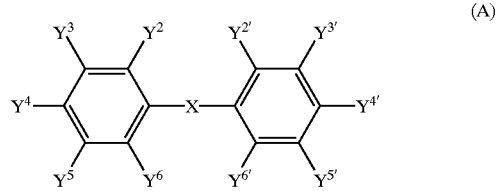

or a pharmaceutically acceptable salt, hydrate or solvate thereof, wherein at least one of Y or Y' is OH;

the others Y and Y' are independently selected from the group consisting of hydrogen, halogen, hydroxy, methoxy, and nitro; and

X=S.

16. The method of claim 15, wherein the diabetic complications comprise diabetic neuropathy, diabetic cataract and retinopathy, diabetic corneal keratopathy, diabetic nephropathy, diabetic dermopathy and other diabetic microangiopathies.

17. A method of preventing diabetic complications in mammals comprising the administration of a compound represented by the following general formula (A)

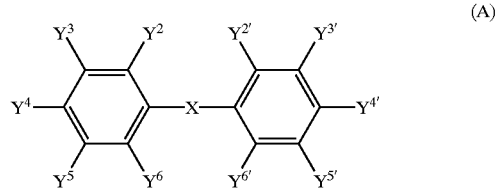

or a pharmaceutically acceptable salt, hydrate or solvate thereof, wherein at least one of Y or Y' is OH;

the others Y and Y' are independently selected from the group consisting of hydrogen, halogen, hydroxy, methoxy, and nitro; and X is selected from the group consisting of O, S, ketone, and a single bond directly linking both substituted benzyl groups.

18. The method of claim 17, wherein the diabetic complications comprise diabetic neuropathy, diabetic cataract and retinopathy, diabetic corneal keratopathy, diabetic nephropathy, diabetic dermopathy and other diabetic microangiopathies.

19. A method of preventing diabetic complications in mammals comprising the administration of a compound represented by the following general formula (A)

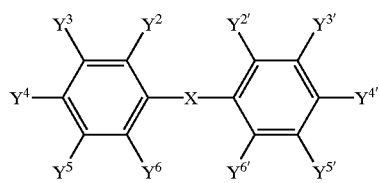

(A)

or a pharmaceutically acceptable salt, hydrate or solvate thereof, wherein at least one of Y or Y' is OH;

at least one of Y or Y' is a halogen;

the others Y and Y'0 are independently selected from the group consisting of hydrogen, halogen, hydroxy, methoxy, and nitro; and X is selected from the group consisting of O, S, ketone, and a single bond directly linking both substituted benzyl groups.

20. The method of claim 19, wherein the diabetic complications comprise diabetic neuropathy, diabetic cataract and retinopathy, diabetic corneal keratopathy, diabetic nephropathy, diabetic dermopathy and other diabetic microangiopathies.

21. A method of preventing diabetic complications in mammals comprising the administration of a compound represented by the following general formula (A)

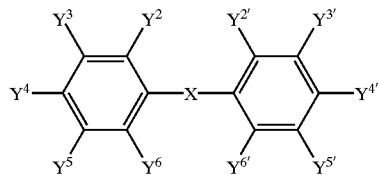

(A)

or a pharmaceutically acceptable salt, hydrate or solvate thereof, wherein at least one of Y or Y' is OH;

the others Y and Y' are independently selected from the group consisting of hydrogen, halogen, hydroxy, methoxy, and nitro; and

X=O.

22. The method of claim 21, wherein the diabetic complications comprise diabetic neuropathy, diabetic cataract and retinopathy, diabetic corneal keratopathy, diabetic nephropathy, diabetic dermopathy and other diabetic microangiopathies.

23. A method of preventing diabetic complications in mammals comprising the administration of a compound represented by the following general formula (A)

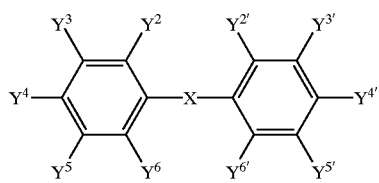

(A)

or a pharmaceutically acceptable salt, hydrate or solvate thereof, wherein at least one of Y or Y' is OH;

the others Y and Y' are independently selected from the group consisting of hydrogen, halogen, hydroxy, methoxy, and nitro; and X is a single bond directly linking both substituted benzyl groups.

24. The method of claim 23, wherein the diabetic complications comprise diabetic neuropathy, diabetic cataract and retinopathy, diabetic corneal keratopathy, diabetic nephropathy, diabetic dermopathy and other diabetic microangiopathies.

25. A method of preventing diabetic complications in mammals comprising the administration of a compound represented by the following general formula (A)

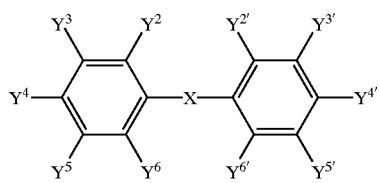

(A)

or a pharmaceutically acceptable salt, hydrate or solvate thereof, wherein at least one of Y or Y' is OH;

the others Y and Y' are independently selected from the group consisting of hydrogen, halogen, hydroxy, methoxy, and nitro; and

X=S.

26. The method of claim 25, wherein the diabetic complications comprise diabetic neuropathy, diabetic cataract and retinopathy, diabetic corneal keratopathy, diabetic nephropathy, diabetic dermopathy and other diabetic microangiopathies.

* * * * *